United States Patent [19]

Bayer et al.

[11] Patent Number: 5,973,124
[45] Date of Patent: Oct. 26, 1999

[54] MODIFIED AVIDIN AND STREPTAVIDIN MOLECULES AND USE THEREOF

[75] Inventors: Edward A. Bayer, Raanana; Meir Wilchek, Rehovot; Ely Morag, Tel-Aviv, all of Israel

[73] Assignee: Yeda Research and Development Co. Ltd., Rehovot, Israel

[21] Appl. No.: 08/973,970

[22] PCT Filed: Jun. 13, 1996

[86] PCT No.: PCT/IL96/00014

§ 371 Date: Mar. 5, 1998

§ 102(e) Date: Mar. 5, 1998

[87] PCT Pub. No.: WO97/00329

PCT Pub. Date: Jan. 3, 1997

[30] Foreign Application Priority Data

Jun. 14, 1995 [IL] Israel ..................................... 114149

[51] Int. Cl.⁶ .......................... C07K 14/77; G01N 33/532
[52] U.S. Cl. ................................ 530/402; 435/6; 435/7.5; 435/188; 436/526; 436/527; 436/531; 530/367; 530/405
[58] Field of Search .................................. 435/6, 7.4, 7.5, 435/21, 28, 188; 436/519, 531, 526, 527; 530/367, 391.1, 402, 405

[56] References Cited

U.S. PATENT DOCUMENTS 5,863,740 1/1999 Kientsch-Engel et al. .............. 435/7.5

OTHER PUBLICATIONS

C. Argarana et al., "Molecular cloning and nucleotide sequence of the streptavidin gene", Nucleic Acids Research, vol. 14, No. 4, pp. 1872–1882, 1986.

E. Bayer et al., "Avidin–Biotin Technology: Preparation of Biotinylated Probes", Method in Molecular Biology, Chapter 13, vol. 10, pp. 137–142, 1992.

E. Bayer et al., "Avidin–Biotin Technology: Preparation of Biotinylated Probes", Method in Molecular Biology, Chapter 14, vol. 10, pp. 143–148, 1992.

G. Gitlin et al., "Studies on the biotin–binding site of avidin: Lysine residues involved in the active site" Biochem. J., vol. 242, pp. 923–926, 1987.

G. Gitlin et al., "Studies on the biotin–binding site of avidin: Tryptophan residues involved in the active active site", Biochem. J., vol. 250, pp. 291–294, 1988.

G. Gitlin et al., "Studies on the biotin–binding site of avidin: Tryptophan residues involved in the active active site", Biochem. J., vol. 256, pp. 279–282, 1988.

G. Gitlin et al., "Studies on the biotin–binding sites of avidin and streptavidin: A chemically induced dynamic nuclear polarization of the status of tyrosine residues", Biochem. J., vol. 259, pp. 493–498, 1989.

G. Gitlin et al., "Studies on the biotin–binding sites of avidin and streptavidin: Tyrosine residues are are involved in the binding site", Biochem J., vol. 269, pp. 527–530, 1990.

N. Green, "Avidin", Adv. Protein Chem., vol. 29, pp. 85–133.

E. Katchalski–Katzir, "Immobilized enzymes: Learning from past successes and failures", Trends in Biotechnology, vol. 11, No. 11, pp. 471–478, Nov. 1993.

J. Riordin, "Tetranitromethane. A reagent for the Nitration of Tyrosine and Tyrosyl Residues of Proteins", Journal of the American Chemical Society, vol. 88, No. 17, pp. 4104–4105, Sep. 5, 1966.

J. Scott, "Discovering peptide litgands using epitope libraries", TIBS, vol. 17, pp. 241–245, Jul. 1992.

M. Suter et al., "Isolation and characterization of highly purified streptavid obtained in a two–step purification procedure from *Streptomyces avidinii* grown in a synthetic medium", Journal of Immulogical Methods, vol. 113, pp. 83–91, 1988.

P. Webber et al., "Structural origins of high–affinity biotin binding to streptavidin" Science, vol. 243, pp. 85–88, Jan. 6, 1989.

M. Wilchek et al, "The avidin–biotin complex in bioanalytical applications", Analytical Biochemistry, vol. 171 pp. 1–32, 1988.

E. Bayer et al., "Application of avidin–biotin technology to affinity–based separations" Journal of Chromatography, vol. 510, pp. 3–11, 1990.

P. Vincent et al, "A comparison of the binding of biotin and biotinylated macromolecular lignads to an anti–biotin monoclonal antibody and to streptavidin", Journal of Immunological Methods, vol. 165, pp. 177–182, 1993.

E. Morag et al. "Immobilized Nitro–avidin and Nitro–streptavidin as reusable affinity matrices for applications in avidin–biotin technology", Analytical Biochemisry, vol. 243, No. 0515, pp. 257–263, 1996.

M. Balass et al., "Recovery of high–affinity phage from a nitrostreptavidin matrix in phage–display technology", Analyticle Biochemistry, vol. 243, No. 0515, pp. 264–269, 1996.

*Primary Examiner*—Mary E. Ceperley
*Attorney, Agent, or Firm*—Browdy and Neimark

[57] ABSTRACT

Biotin-binding modified avidin-type molecules are provided in which the essential tyrosine residue in the biotin-binding site is modified in such a way that its pKa is decreased in comparison to the pKa of the unmodified tyrosine residue in the corresponding unmodified avidin-type molecule. The avidin-type molecules include: (i) native egg-white avidin; (ii) recombinant avidin; (iii) deglycosylated forms of avidin; (iv) bacterial streptavidin; (v) recombinant streptavidin; (vi) truncated streptavidin; and (vii) derivatives of (i)–(vi) which are modified at sites other than the essential tyrosine residue. The modification is achieved by substitution at one or both ortho positions to the hydroxy radical of the tyrosine residue by radicals such as nitro, halogen, azo and amino. The modified avidin-type molecules can be used in all applications of the avidin-biotin technology.

28 Claims, 8 Drawing Sheets

MODIFIED AVIDIN AND STREPTAVIDIN MOLECULES AND USE THEREOF

FIELD AND BACKGROUND OF THE INVENTION

The present invention relates to an avidin-type molecule which is modified at the binding-site tyrosine residue, known to be critical to the binding of biotin. The modified avidin is still capable of binding biotin or a biotinylated ligand under specific conditions, but upon altering these conditions, for example, high pH or competition with biotin, the bound biotin moiety or biotinylated ligand is removed. The invention thus provides a reversible form of avidin for use in avidin-biotin technology, thus "correcting" one of the major disadvantages of the avidin molecule for various applicative purposes, i.e., the extreme denaturing conditions required to disrupt the avidin-biotin complex. These drastic conditions necessary to dissociate the avidin-biotin complex usually inactivate irreversibly the biological activity of the biotinylated component, thus rendering it unsuitable for subsequent use.

Avidin (from egg-white) and streptavidin (from *Streptomyces avidinii*) are two related proteins that bind biotin with similar dissociation constants of about $10^{-15}$M (Green, 1975). In addition to the binding of biotin, many of their physical properties are quite similar. Both, for example, are constructed of four non-covalently attached identical subunits, each of which bears a single biotin-binding site. The subunit $M_r$ values are also very similar. Moreover, several short stretches in the sequences of the two proteins are preserved, particularly to Trp-Lys stretches that occur at approximately similar positions (Argarana et al., 1986). We have previously shown (Gitlin et al., 1987, 1988a) that certain lysine and tryptophan residues are involved in the biotin binding in both proteins (Gitlin et al., 1988b). More recently, it was shown that both avidin and streptavidin exhibit the same three dimensional fold, and the most of the binding site residues are identical or similar (Weber et al., 1989). The binding site geometry and bonds formed between both proteins with the biotin molecule are indeed very similar.

Despite these similarities, several differences exist between the two proteins. Avidin is a disulphide-bridged glycoprotein containing two methionine residues, whereas streptavidin is not glycosylated and is devoid of sulphur-containing amino acid side chains. Another significant difference is in the tyrosine content. Avidin has only one tyrosine residue (Tyr-33), whereas streptavidin has six tyrosine residues at positions 22, 43, 54, 60, 83 and 96. Interestingly, the single tyrosine residue of a avidin is located in a region which contains a sequence identical with that of one of the streptavidin tyrosine residues (Tyr-43 in the stretch Thr-Gly-Thr-Tyr). This tyrosine residue occupies a prominent position in the biotin-binding site and the chemical modification of the tyrosine hydroxyl group leads to irreversible inactivation of the avidin molecule (Gitlin et. al., 1990).

Each avidin monomer binds one molecule of biotin. The unique feature of this binding, of course, is the strength and specificity of formation of the avidin-biotin complex. The resultant affinity constant, estimated at $1.6 \times 10^{15}$ $M^{-1}$ for avidin and $2.5 \times 10^{13}$ $M^{-1}$ for streptavidin (Green, 1990), is the highest known for a protein and an organic ligand. It is so strong that biotin cannot be released from the binding site, even when subjected to a variety of drastic conditions such as high concentrations of denaturing agents at room temperature, e.g., 6M guanidinium hydrochloride, 3M guanidinium thiocyanate, 8M urea, 10% β-mercaptoethanol or 10% sodium dodecyl sulfate. Under combined treatment with guanidinium hydrochloride at low pH (1.5) or upon heating (>70° C.) in the presence of denaturing agents or detergents, the protein is denatured, and biotin is dislodged from the disrupted binding site.

Avidin recognizes biotin mainly at the ureido (urea-like) ring of the molecule. The interaction between the binding site of avidin with the sulfur-containing ring of the valeric acid side chain of the vitamin is of much lower strength. The relatively weak interaction between the carboxy-containing side chain of biotin and avidin means that the former can be modified chemically and attached to a wide variety of biologically active material; the biotin moiety of the resultant derivative or conjugate is still available for interaction with avidin. In turn, the avidin can be derivatized with many other molecules, notably "probes" or reporter groups of different types.

This is the crux of avidin-biotin technology (Wilchek and Bayer, 1990). Thus, a biologically active target molecule in an experimental system can be "labeled" with its biotinylated counterpart (a binder), and the product can then be subjected to interaction with avidin, either derivatized or conjugated with an appropriate probe.

The use of the egg-white avidin in the avidin-biotin technology is sometimes restricted due to the high basicity (pI~10.5) and presence of sugar moieties on the avidin molecule, which may lead to nonspecific or otherwise undesired reactions. In recent years, the bacterial protein streptavidin, has largely replaced egg-white avidin for most applications in avidin-biotin technology. However, the problems with streptavidin (high cost and biotin-independent cell binding) has prompted renewed interest in egg-white avidin as the standard for avidin-biotin technology. For this purpose, modified avidins exhibiting improved molecular characteristics both over the native protein (and previous derivatives thereof) as well as over streptavidin, have been prepared, such as N-acyl avidins, e.g., N-formyl, N-acetyl and N-succinyl avidins. These derivatives of avidin reduce the charge of the protein, but they are all prepared via covalent attachment to the available lysines of avidin, and the consequent blocking of the free amino groups hinders subsequent preparation of other types of conjugates (notably protein-protein conjugates such as avidin-labeled enzymes) which are often prepared by crosslinking via lysine residues using bifunctional reagents (e.g., glutaraldehyde).

A more useful and effective alternative to lysine modification is the modification via arginines. In this case, the pI of the protein is efficiently reduced and the lysines are still available for subsequent interaction. Two different derivatives of avidin which are modified in this manner are commercially available. One, ExtrAvidin®, can be obtained in various functionally derivatized or conjugated forms from Sigma Chemical Company (St. Louis, Mo.). A second, NeutraLite Avidin™ (a product of Belovo Chemicals, Gastogne, Belgium) is additionally modified and can be purchased in bulk quantities.

Although the reduction of the pI of egg-white avidin solves one of the problems, the presence of the oligosaccharide residue remains a serious source of nonspecific (biotin-independent) interaction which restricts its application. The return of egg-white avidin as the standard for avidin-biotin technology has been contingent upon the removal of its sugars.

The possibilities for removing a sugar from a glycoprotein are quite limited; it is possible to do so either chemically or enzymatically. The chemical methods currently available, e.g., using HF or periodate oxidation, are either destructive or inefficient. The well known enzymatic method, which employs N-glycanase (Tarentino et al., 1984), is usually very expensive and not very effective for avidin when conventional methodology is used. Eventually, a viable procedure for deglycosylation was established and the resultant product was subsequently modified chemically via the arginines and is known under the trade mark NeutraLite Avidin™ (Belovo Chemicals).

In spite of these improvements, one of the main problems in the several applications of the avidin-biotin technology is the lack of reversibility of the binding and the difficulty of separating the avidin and the biotin moieties at the end of the process, without denaturation of the avidin or damaging or inactivating the biological material which had been attached via the biotin bridge. Alternatively, it would be advantageous (particularly for industrial use) to remove damaged or inactivated material from an avidin column, thus reconstituting the column for attachment of the new sample of biotinylated component.

It is an object of the present invention to provide modified avidins which are still biotin-binding and can be advantageously used in methods employing the avidin-biotin technology in which reversibility of the method is desired or is an advantage.

Nitration of tyrosine residues in model peptides and proteins using tetranitromethane has been described (Riordan et al., 1966; Sokolovsky et al., 1967). In a previous work of the present inventors (Gitlin et al., 1989), a nitrotyrosine derivative of avidin was prepared by nitration of egg-white avidin dissolved in 9M-urea with tetranitromethane (TNM). The resultant nitro-avidin preparation was inactive, i.e. it failed to bind biotin, because the nitration was carried out on a denatured form of avidin (in the presence of urea). The nitro-avidin thus prepared is entirely inadequate for use in avidin-biotin technology.

$^{125}$I-labelled avidin and streptavidin have been prepared for analytical purposes. The single tyrosine residue of each avidin subunit is not readily accessible to iodination. Avidin is rendered susceptible to iodination (chloramine T method) by the introduction of 3-(p-hydroxyphenyl)propionyl groups and thus $^{125}$I-labelled avidin containing said groups was prepared. $^{125}$I-labelled Bolton-hunter reagent can also be employed to label avidin (Finn and Hofmann, 1985). $^{125}$I-streptavidin was produced by iodination of streptavidin with Na$^{125}$I using the iodogen method (Suter et al., 1988). Unlabelled iodinated avidin and streptavidin have not been described heretofore.

Azotization and amination of tyrosine residues in model peptides and proteins, e.g. ribonuclease A, has been previously described (Gorecki et al., 1971; Sokolovsky et al, 1967).

SUMMARY OF THE INVENTION

The present invention relates to a biotin-binding modified avidin-type molecule selected from the group of molecules comprising: (i) native egg-white avidin; (ii) recombinant avidin; (iii) deglycosylated forms of avidin; (iv) bacterial streptavidin; (v) recombinant streptavidin; (vi) truncated streptavidin; and (vii) derivatives of (i)–(vi) which are modified at sites other than the essential tyrosine residue, characterized in that in said biotin-binding modified avidin-type molecule the essential tyrosine residue in the biotin-binding site is modified in such a way that its pKa is decreased in comparison to the pKa of the unmodified tyrosine residue in the corresponding unmodified avidin-type molecule.

The modified avidin-type molecule of the invention has one or more electrophilic and/or nucleophilic groups on the essential tyrosine residue of the avidin-type molecule, and may be exemplified by compounds wherein the modified tyrosine is of the formula:

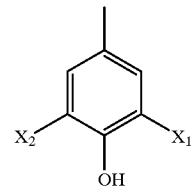

wherein $X_1$ and $X_2$ are each a radical selected from nitro, halogen, $NR_1R_2$ and $-N=NR_3$ in which $R_1$ and $R_2$ are each selected from hydrogen, $C_1-C_8$ alkyl and $C_1-C_6$ carboxylic acyl, and $R_3$ is aryl substituted by an acidic radical.

In one preferred embodiment of the invention, the avidin-type molecule is modified by addition of one or more electrophilic groups on the tyrosine residue. For example, avidin or streptavidin may be modified by nitration or halogenation, preferably iodination, of the tyrosine residue, as depicted in FIG. 1 ($X_1$ or $X_2$ is $NO_2$ or halogen, preferably I), thus decreasing the pKa of the tyrosine residue in the biotin-binding site from 10.5–12.5 to 6.5–8.5, preferably to about 7.0

Such modification of the tyrosine residue in the avidin-type molecule involves the addition of one or more electrophilic group(s) at the ortho position(s) (adjacent to the hydroxyl group) on the tyrosine ring. As an example of this type of modified avidin, the nitration of the tyrosine residue using tetranitromethane (TNM) was employed. The resultant nitrotyrosine-containing avidin and streptavidin, hereinafter referred to as "nitro-avidin" and "nitro-streptavidin", respectively, have been studied extensively in order to define relatively mild conditions for releasing the biotin moiety or the biotinylated ligand, e.g., a biotinylated antibody, enzyme, nucleic acid or cell.

In the present invention, the nitration of avidin was performed under nondenaturing conditions, and the resultant nitro-avidin and nitro-streptavidin were shown to bind a biotinylated ligand efficiently and tightly at pH 4. When the pH was elevated to 8, the biotinylated ligand was still retained on the column. However, when the pH was elevated to 10, the biotinylated ligand was released. Alternatively, at lower pH (e.g., between the range of pH 4 to 8), the biotinylated ligand could be released by exchange using free biotin. These characteristics of the nitro-avidin and the nitro-streptavidin provide forms of avidin and streptavidin which are appropriate for variety of applications. These materials have been used according to the present invention for the binding and subsequent release of several examples of biotinylated ligands to nitro-avidin and nitro-streptavidin immobilized onto a Sepharose resin as well as for the attachment and release of biotinylated ligands to nitro-avidin and nitro-streptavidin adsorbed to microtiter plates.

In another embodiment the present invention relates to halogenated, more preferably to unlabelled iodinated avidin or streptavidin. Iodination of the tyrosine residue in avidin or streptavidin with KI using the chloramine T procedure, yielded mono- and/or diiodotyrosine-avidin or -streptavidin, shown also to be effective reversible forms of avidin.

A further embodiment of the invention regards avidin-type molecules modified at the essential tyrosine residue by one or more nucleophilic groups selected from $NR_1R_2$ and $-N=NR3$.

In the azo derivatives of the invention, i.e. the compounds wherein $X_1$ and/or $X_2$ is —N=NR$_3$, $R_3$ is aryl, preferably carbocyclic aryl, most preferably, phenyl, substituted by an acidic radical selected from carboxyl and a residue of an inorganic acid such as phosphoric, arsonic or sulfonic acid.

The azo derivatives according to the invention are prepared from the corresponding p-amino derivatives, e.g. p-arsanilic acid, anthranilic acid, p-aminobenzoic acid, sulfanilic acid and p-aminophosphoric acid, by diazotization with NaNO$_2$ and reaction of the resulting diazonium salt with the avidin-type molecule of choice.

In the amino derivatives of the invention, i.e. the compounds wherein $X_1$ and/or $X_2$ is NR$_1$, $R_2$, $R_1$ and $R_2$ are each selected from H, alkyl and acyl. The alkyl radical is preferably a $C_1$–$C_8$ straight or branched alkyl, examples being methyl, ethyl, propy, isopropy, butyl, hexyl, octyl. The acyl radical is preferably a $C_1$–$C_6$ carboxylic acyl such as acetyl, propionyl, butyryl, succinyl, or benzyloxycarbonyl.

The amino derivatives of the invention may be prepared by reduction of the corresponding azo derivatives with sodium hydrosulfite Na$_2$S$_2$O$_4$ or by reduction of the corresponding nitro derivatives with Na$_2$S$_2$O$_4$ and, if desired, the amino group is further alkylated or acylated by standard methods.

The modified avidin-type molecules of the present invention can be used in the very many applications of the avidin-biotin technology.

BRIEF DESCRIPTION OF THE DRAWINGS

In FIG. 11 A, identical samples of biotinylated BSA were applied successively (at pH 4 using Buffer A) to, and eluted (at pH 10 using Buffer C) from, a column containing a Sepharose-nitro-avidin resin. FIG. 11 B shows that accumulation of the eluted fractions gave essentially identical levels of protein bound and eluted per cycle.

DETAILED DESCRIPTION OF THE INVENTION

The term "avidin-type molecule" as used herein refers to the native egg-white glycoprotein avidin, to deglycosylated forms of avidin, to bacterial streptavidins produced by selected strains of Streptomyces, e.g., *Streptomyces avidinii*, to truncated streptavidins, and to recombinant avidin and streptavidin as well as to derivatives of native, deglycosylated and recombinant avidin and of native, recombinant and truncated streptavidin, which are modified at sites other than the essential tyrosine, for example, N-acyl avidins, e.g., N-acetyl, N-phthalyl and N-succinyl avidin, and the commercial products ExtrAvidin™ and Neutralite Avidin™.

All forms of avidin-type molecules are encompassed by the present invention, both native and recombinant avidin and streptavidin as well as derivatized molecules, e.g. nonglycosylated avidins, N-acyl avidins and truncated streptavidins. Some of these materials are commercially available, e.g. native avidin and streptavidin, nonglycosylated avidins, N-acyl avidins and truncated streptavidin, or can be prepared by well-known methods (see Green, 1990, for preparation of avidin and streptavidin; Hiller et al., 1990, for preparation of non-glycosylated avidin; Bayer et al., 1990, for the preparation of streptavidin and truncated streptavidin). Recombinant avidin and streptavidin can be prepared by standard recombinant DNA techniques, for example, as described by Chandra and Gray, 1990, for recombinant avidin, and by Argarana et al., 1986, for recombinant streptavidin.

The "biotinylated ligands" that can be used with the modified avidins of the invention in methods of application of the avidin-biotin technology, are biotinylated forms of desired ligands such as proteins, e.g. glycoproteins, gangliosides, heparin, polysaccharides, or nucleic acids, i.e. DNA and RNA, or phages, viruses, bacterial and other cells, wherein said ligands are covalently linked to biotin or to a homolog, analog or derivative thereof. Many biotinylated ligands are commercially available or can be prepared by standard methods (see, for example, Bayer and Wilchek, 1992a).

Figure 1:
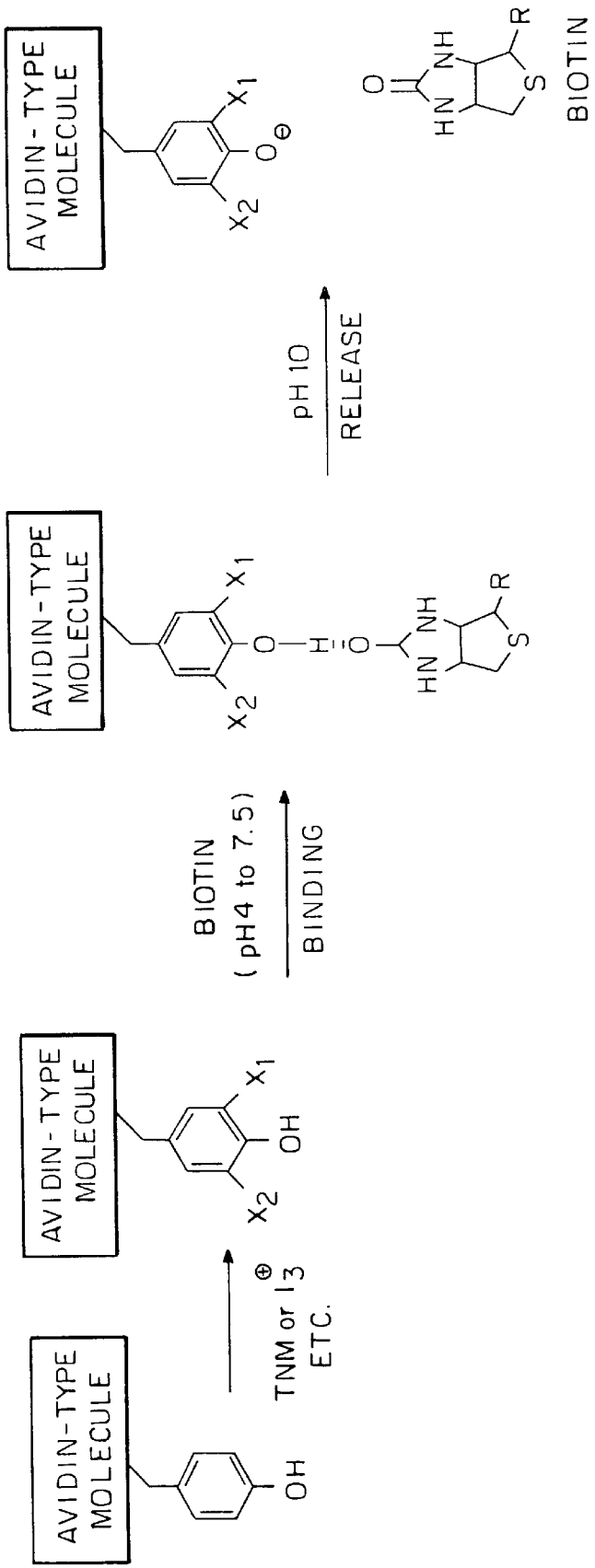
FIG. 1 shows a reaction scheme for preparation of a tyrosine-modified avidin-type molecule of the invention and its use in a reversible method using avidin-biotin technology.

The modified avidin-type molecules of the invention, mainly avidin and streptavidin derivatives modified at one or both ortho positions of the binding-site tyrosine residue (see FIG. 1), are suitable for reversible interaction with the biotin moiety, and thus constitute important new tools for avidin-biotin technology.

These modified avidin-type molecules allow to remove, under mild conditions, free biotin and/or biotinylated ligands, e.g. biotinylated enzymes and other biotinylated biologically active materials, from immobilized ortho-phenol-modified avidin-type molecules or from soluble complexes which comprise the modified avidin together with the biotinylated ligand in solution. Such mild conditions may consist of excess concentrations of biotin, high pH, e.g. pH 10, relatively low nondenaturing concentrations of urea, guanidine or thiocyanate, heat and/or combinations thereof. In one preferred embodiment, removal of the biotin or the biotinylated moiety from the immobilized modified avidin is carried out by change of the pH, for example raising the pH to 10. In another preferred embodiment, removal is carried out by adding an excess of biotin, for example, a solution of 0.6 mM biotin is passed through the modified avidin column to displace the biotinylated component.

The modified avidin-type molecules of the invention are suitable for use in any method employing the avidin-biotin technology, particularly in those methods wherein reversibility of the avidin-biotin binding is an advantage, for example, as reversible immobilization columns for use in affinity chromatography for removal of affinity ligands; to remove immobilized enzymes thus creating a reversible enzyme reactor; to disrupt soluble biological complexes in solution consisting of biotinylated material crosslinked via an avidin bridge; to produce high-afinity phase libraries; and for use in cell separation, thus facilitating the release of a viable or intact cell together with the recognition component or ligand, e.g. antibody, from a resin, or to counteract agglutination of such cells by dissociating the avidin bridge.

The invention also relates to a modified avidin-type molecule of the invention attached to a solid support or matrix. Any solid support used in the art is suitable such as, but not limited to, resins, microtiter plates, glass beads, magnetic beads and the like. The attachment of the avidin to the solid support may be covalent or noncovalent and is carried out by standard methods. In one preferred embodiment, the modified avidin-type molecule is immobilized onto a resin, preferably Sepharose, and the thus obtained Sepharose-nitro-avidin affinity resin may be poured into a column for isolation procedures (Bayer and Wilchek, 1992b). In the description herein the term "avidin-Sepharose column" will be used for a column that contains a modified avidin-type molecule of the invention immobilized onto a Sepharose resin. These columns are useful particularly for separation procedures.

In another embodiment of the invention, the modified avidin-type molecule is attached to wells of microtiter plates.

In the well-known affinity chromatography procedure, which is the prototype of all affinity methodologies, a binding ligand, e.g., an antibody or receptor, is attached to a solid support, such as Sepharose. This can be accomplished by biotinylation of the said ligand, and subsequent immobilization to Sepharose via an avidin or streptavidin bridge. The resultant avidin-Sepharose column is then used as a handle to isolate and purify material which interacts with said biotinylated ligand. In many cases, it would be advantageous to separate the biotinylated ligand from the avidin-Sepharose column, either to recover the ligand itself, which might be precious or delicate in nature, or to reconstitute the column for alternative usage. This can be accomplished by using a column which contains a modified avidin-type molecule of the present invention to immobilize the biotinylated ligand, which can eventually be released from the column by addition of either alkaline solutions (e.g., Buffer C, pH 10) or by adding excess biotin (e.g., 0.6 mM at any pH). Either a new type of biotinylated ligand or a fresh batch of the same biotinylated ligand can then be added to the reconstituted avidin column.

The avidin-biotin system has been used to separate cells by a variety of methods. One approach is to use a biotinylated ligand (e.g., antibody) which recognizes a cell surface molecule (e.g., surface antigen). The biotinylated ligand can be bound to a column or other type of matrix, such as magnetic beads, via an avidin or streptavidin bridge. Alternatively, a suspension of a mixed cell population ca be treated with the biotinylated ligand and the cells bearing the interacting surface molecule can be agglutinated using avidin in solution. Commonly, this approach has been used simply to selectively "remove" a given population of cells from the mixed population. Once bound to the matrix or agglutinated by avidin, the affinity interactions involved (i.e., between the biotinylated ligand and surface molecule, and between the avidin and biotin) cannot be easily disrupted, in a manner which would preserve cell integrity or viability. For example, disruption of the interaction between an antibody and an antigen usually requires conditions, such as low pH, which are damaging to most cells. The non-interacting cells, however, can be recovered. In order to recover the bound cell population, a column containing a modified avidin-type molecule of the present invention can be used and a biotin-containing solution (e.g., 0.6 mM of biotin under isotonic conditions, e.g., 0.15M NaCl at pH 7, or such excess concentrations of biotin in a suitable tissue-culture medium) can be used to release the cells (together with the biotinylated ligand) from the column or the agglutinated cells can be dispersed using the same biotin-containing solution.

Immobilized enzymes are largely used in the food, pharmaceutical and chemical industries (Katchalsky-Katzir, 1993). One of the problems with immobilized enzymes for use in enzyme reactor systems is that the enzyme or its matrix undergoes a type of aging process. For example, enzymes are notoriously sensitive proteins, they often have a definitive half-life, and, in time, they may be inactivated either during use or upon storage. For industrial usage, it would thus be advantageous to reuse the immobilizing matrix once the bound enzyme has become useless. An enzyme reactor consisting of a biotinylated enzyme bound to a column containing a modified avidin-type molecule according to the present invention can thus be reconstituted by removing the inactivated biotinylated enzyme by addition of either alkaline solutions (e.g., Buffer C, pH 10) or by adding excess biotin (e.g., 0.6 mM at any pH). A fresh batch of biotinylated enzyme can then be added to the reconstituted modified avidin column.

Similarly, cells can be immobilized to a modified avidin column and used as a cellbased reactor system. The cells can be released using a biotin-containing solution (e.g., 0.6 mM of biotin under isotonic conditions, e.g., 0.15M NaCl at pH 7, or such excess concentrations of biotin in a suitable tissue-culture medium), and the modified avidin column can be thus reconstituted.

In the phage library technique, a binding ligand (e.g., antibody, receptor) is attached to a solid support such as a microtiter plate. This is often accomplished by biotinylation of the said ligand, and subsequent immobilization to the plate via a streptavidin bridge. Filamentous bacteriophages (e.g., M13) are then added, and those phages, which contain surface peptides that are capable of interacting with the immobilized ligand, thus bind to the plate. Unspecifically bound phages are removed by washing with low concentrations of neutral detergents such as Tweeen 20. The bound phages are subsequently released from the plate, usually by reducing the pH which disrupts the interaction between the immobilized ligand and the surface peptides on the phage. One of the potential problems in this approach is that some phages may still be bound to the plate via very high affinity interactions. These phages would be of interest specifically due to their high affinity peptides to the biotinylated ligand. Thus, by using the modified avidin or streptavidin of the present invention, the high affinity phages can be released from the microtiter-plates together with the biotinylated ligand, by addition of either alkaline solutions (e.g., Buffer C, pH 10) or by adding excess biotin (e.g. 0.6 mM at any pH). The recovered high-affinity peptides bound to the phage can then be enriched by subsequent infection of bacteria, and by established phage library procedures (see, for example, Scott, 1992).

Gene enrichment and DNA isolation can be achieved by complexing biotinylated DNA with a modified avidin-type molecule or a modified avidin column according to the present invention by known methods (see Wilchek and Bayer, 1988). In the past, proteolytic enzymes, such as proteinase K, have been used to digest the avidin in order to free the biotinylated DNA from the complex. Using the modified avidin-type molecule of the present invention, the biotinylated DNA can be released using alkaline solutions (e.g., Buffer C, pH 10) or by adding excess biotin (e.g., 0.6 mM at any pH).

Biosensors consist of biological-sensing element which confers specificity and a transduction function (i.e., electrochemical, optical, calorimetric or acoustic) which covers a biological event into a response that can be further processed and quantified. The biological ligand can either be catalytic (e.g., enzymes, bacterial cells, tissues) or noncatalytic (e.g., antibodies, receptors, DNA). Such detectors rely on the immobilization of one of the interacting components onto the sensing surface, and the resultant constituents of the completed biosensing apparatus are notably expensive. The avidin-biotin system has been used in the past as a general method for immobilizing such ligands onto biosensors. The capacity to replace the native avidin or strepavidin with the modified avidins according to the present invention, would provide a reversible type of biosensor which would be an advantage in cost and convenience. Thus, the biotinylated ligand can be immobilized to the biosensor via the modified avidin or streptavidin, and when desired the biorunylated ligand can be released using alkaline solutions (e.g., Buffer C, pH10) or by adding excess biotin (e.g., 0.6 mM of biotin at any desired pH, ionic strength conditions, etc.). The modified avidin-type molecule of the biosensor can then be charged with either the same or a different biotinylated ligand.

The present invention also provides a process for the recovery of either the avidin-column or the biotinylated ligand in a method employing the avidin-biotin technology, which comprises: (i) immobilizing a biotinylated ligand onto a column containing a modified avidin-type molecule of the invention attached to a resin; (ii) carrying out a desired reaction or separation process with the thus immobilized biotinylated ligand; (iii) removing the biotinylated ligand from the immobilized modified avidin column by altering the conditions; and (iv) recovering the biotinylated ligand and/or the modified avidin-column for further use. The biotinylated ligand may be removed from the immobilized modified avidin-column by raising the pH, heating, adding excess concentrations of biotin, or low concentrations of urea, guanidine or thiocyanate, and/or combinations thereof. In preferred embodiments, the biotinylated ligand is removed from the immobilized modified avidin-column by raising the pH to 10, or by adding 0.6 mM biotin.

The invention will now be illustrated by the following non-limiting examples.

EXAMPLES

Materials and Methods
  (i) Materials.
Egg-white avidin was provided by STC labs (Winnipeg, Canada) or from Belovo Chemicals (Bastogne, Belgium). Streptavidin was purified from culture filtrates of *Streptomyces avidinii* using an improved iminobiotin-Sepharose column as described previously (Bayer et al., 1990). Sepharose 4B CL was from Pharmacia (Uppsala, Sweden). Tetranitromethane was from Fluka. Protein A and bovine serum albumin (BSA) were from Sigma Chemical Co. (St. Louis, Mo., USA).
  (ii) Buffers:
Buffer A: 50 mM citrate-phosphate, pH 3–6; Buffer B: 50 mM Tris-HCl, pH7–9; and Buffer C: 50 mM sodium carbonate-HCl, pH 10.
  (iii) Biotinylation Procedures. The proteins and enzymes used in the Examples were biotinylated by conventional biotinylating methods using biotinyl N-hydroxysuccinimide ester (BNHS) as described previously (Bayer and Wilchek, 1990).
  (iv) Immobilization of avidin and streptavidin to Sepharose was carried out by the cyanogen bromide procedure as described previously (Kohn and Wilchek, 1984).
  (v) Enzyme assays.
  (a) Horseradish peroxidase activity Perodixase activity was determined using 2,2' azino-bis (3-ethylbenz-thiazoline-6-sulfonic acid) (ABTS) as substrate. Substrate solution included 2.5 mg of the substrate per 10 ml in Buffer A, pH 5, to which 10 $\mu$l of 30% hydrogen peroxide was added. Color formation was measured at 420 nm.
  (b) Alkaline phosphatase activity was determined using p-nitrophenyl phosphate as substrate. Substrate solution included 10 mg of the substrate dissolved in 10 ml of 1M diethanolamine buffer (pH 9.8) containing 0.5 mM $MgCl_2$. Color formation was measured at 410 nm.
  (vi) Protein.
Protein was determined by the Bradford method using either avidin or streptavidin (where appropriate) or BSA as a standard.

Example 1

Figure 2:
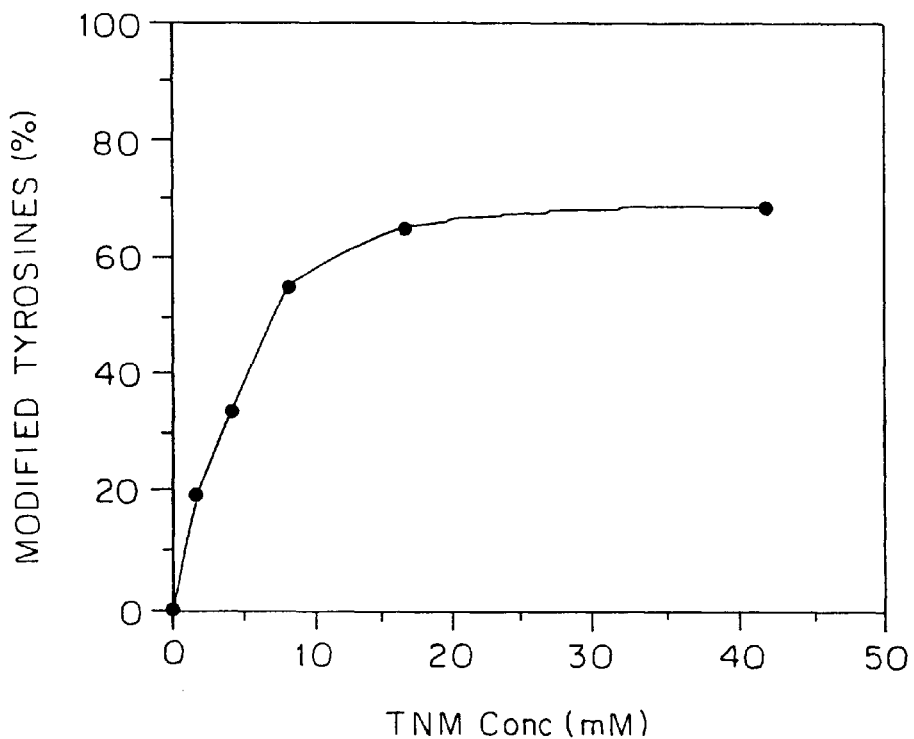
FIG. 2 shows levels (%) of nitration of avidin as a function of tetranitromethane (TNM) concentration (mM), as described in Example 1(i).

Preparation of nitro-avidin, nitro-streptavidin and their immobilization to Sepharose
(i) Preparation of nitro-avidin.
  Samples (5 mg in 1 ml of 50 mM Tris-buffer, at pH 8 or above) or egg-white avidin were treated with different concentrations of tetranitromethane (TNM) (0.5–5 $\mu$l corresponding to about 5–50 mM), for 30 min at 23° C. The samples were dialyzed overnight, once against 1M NaCl and twice against double distilled water. The amount of modified tyrosine in the sample was determined by amino acid analysis. As shown in FIG. 2, under the conditions of the modification procedure, maximum levels (ca. 70%) of modification were achieved using greater than 20 mM concentrations of reagent, i.e., an average of about three out of the four subunits of the avidin tetramer appeared to be modified. In the following experiments, the nitro-avidin used was prepared employing 2 $\mu$.
(ii) Preparation of nitro-streptavidin.
  Streptavidin (2.5 mg per 1 ml buffer) was subjected to nitration using higher levels of tetranitromethane (6 $\mu$l corresponding to about 50 mM), owing to the greater number of tyrosine residues per subunit of the streptavidin molecule.

(iii) Preparation of nitro-avidin and nitro-streptavidin immobilized to Sepharose.

(a) Cyanogen bromide activation of Sepharose 4B CL. 40 g of drained Sepharose 4B CL were washed first with water, then with 30% acetone (v/v) and finally with 60% acetone (v/v). The resin was resuspended in 6 ml of 60% acetone and cooled to 0–4° C. While stirring with a magnetic stirrer, 6 ml of CNBr solution (10 g/100 ml acetone) were added, followed by dropwise addition of an identical volume of triethylamine (TEA) solution (15.2 g/100 ml acetone) for over a period of 1–2 min. The activated resin was filtered and washed with 0.1M sodium bicarbonate.

(b) Immobilization to Sepharose. Coupling of nitro-avidin and nitro-streptavidin to the activated Sepharose 4B CL was performed in 0.1M bicarbonate solution for 16 h at 4° C.

(iv) Nitration of avidin-Sepharose and streptavidin-Sepharose resins.

A sample of 4 ml of avidin-Sepharose resin (1.4 mg avidin/ml Sepharose) prepared as described in (iii))(b) above but using unmodified avidin, and streptavidin, respectively was washed by 50 mM Tris-buffer pH 8, and treated with 6 µl of TNM for 50 min at 23° C. The nitro-modified resin was washed first with 1M NaCl, then with double distilled water and finally with PBS.

Figure 3:
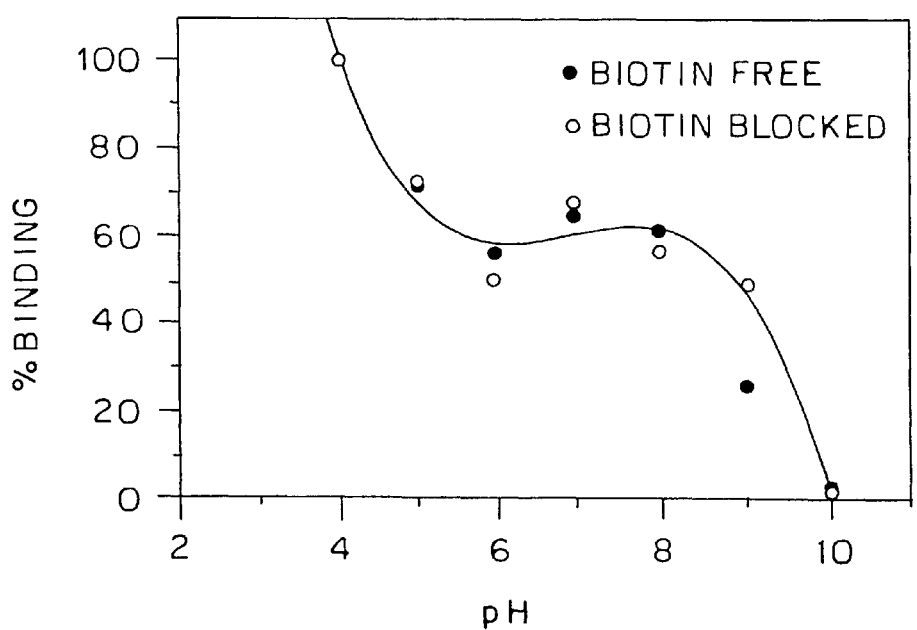
FIG. 3 shows the effect of pH on the binding of biotinylated bovine serum albumine (BSA) to a Sepharose-nitro-avidin resin, as described in Example 2(i).

Example 2
Binding of biotinylated proteins to nitro-avidin (i) The binding of biotinylated proteins to nitro-avidin was tested in several ways. In one experiment, nitro-avidin was immobilized to Sepharose by the cyanogen bromide procedure according to Example 1(iii) using about 0.5 mg avidin per ml Sepharose, and samples of biotinylated BSA in Buffer A, B or C (100 µl) were applied to 100 µl of the nitro-avidin Sepharose resin. The effluent fractions were measured for protein. The percentage of binding at different pH values was determined by subtracting the amount of protein in the effluent fractions from that applied to the resin. As shown in FIG. 3, optimal binding occurred at pH 4. At higher pH (between 5 and 8), plateau levels of binding were observed. Above pH 8, the binding dropped markedly and at pH 10, the binding was negligible.

Figure 4:
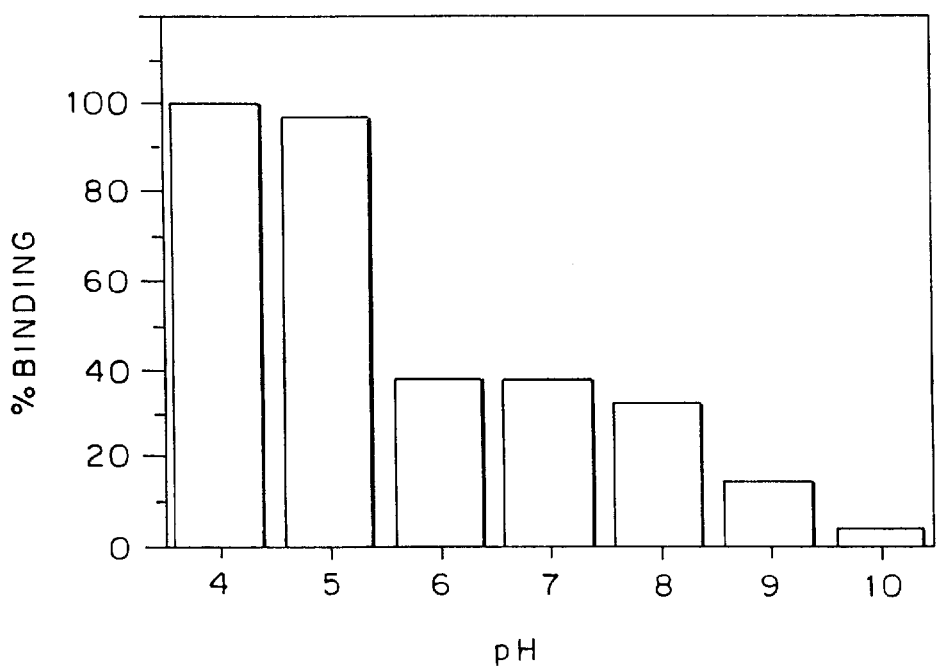
FIG. 4 shows the effect of pH on the binding of biotinylated alkaline phosphatase to microtiter plates containing adsorbed nitro-avidin, as described in Example 2(ii).

(ii) Similar results were achieved using the biotinylated alkaline phosphatase enzyme in a microtiter plate assay (FIG. 4). In this experiment, nitro-avidin prepared according to Example 1(i) was adsorbed to microtiter plates (1 µg nitro-avidin, 100 µl phosphate-buffered saline (PBS)/well), the plates were blocked by a solution of 1% BSA, and samples of biotinylated alkaline phosphatase were applied in Buffers A, B and C of different pH (37 µg/0.1 ml buffer/ well). The plates were washed and the bound enzymatic fraction was determined colorimetrically by enzyme assay as described in method v(b) above using p-nitrophenyl phosphate as a substrate.

Figure 5:
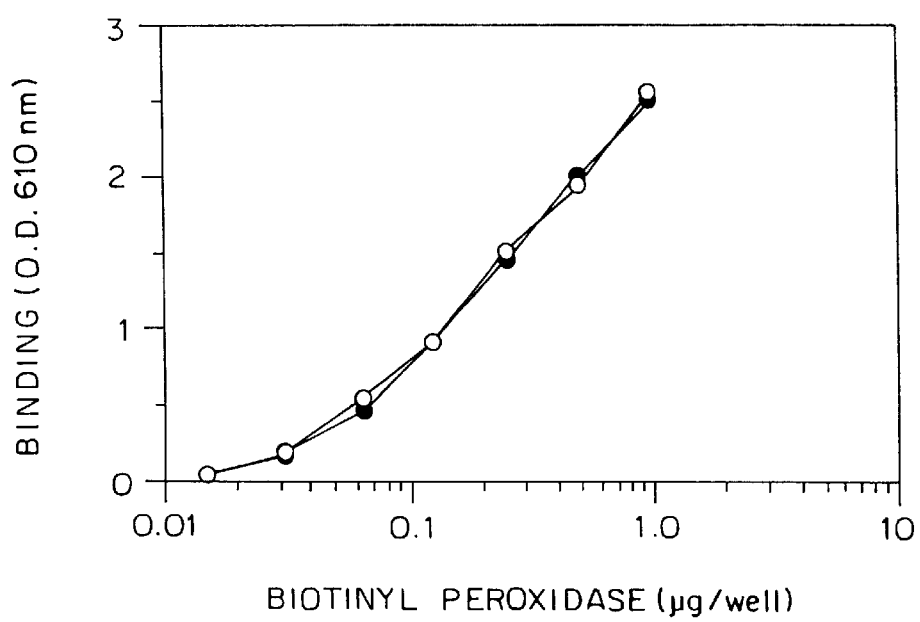
FIG. 5 shows the comparison between biotin-binding activity of avidin (closed circles) and nitro-avidin (open circles), as described in Example 2(iii).

(iii) Using a similar microtiter plate enzyme assay procedure, the binding activity of nitro-avidin was compared with that of native (unmodified) avidin. Microtiter plates, coated with avidin or nitro-avidin (1 µg/100 µl PBS/well), were loaded with different concentrations (between 10 ng and 1 µg in 150 µl of Buffer A) of biotinylated horseradish peroxidase at the experimentally determined, optimal pH for binding (i.e., pH 4). The plates were washed and the peroxidase enzymatic activity was determined as described in method v(a) above using ABTS as a substrate. As shown in FIG. 5, under these conditions, the biotin-binding performance of the unmodified avidin and of nitro-avidin were indistinguishable.

Figure 6:
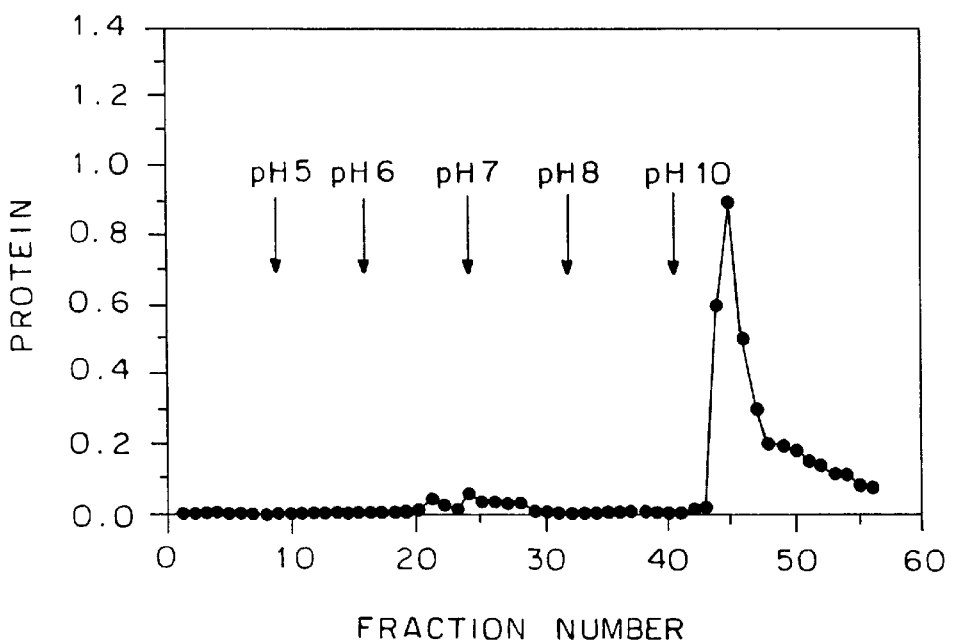
FIG. 6 shows pH-induced release of biotinylated BSA from a Sepharose-nitro-avidin resin, as described in Example 3(i).

Example 3
Release of biotinylated proteins from nitro-avidin (i) In order to determine the preferred conditions for release of biotin from the nitro-avidin column, biotinylated BSA (1.5 mg/150 µl Buffer A, pH 4) was applied to a column containing a nitro-avidin-Sepharose resin according to Example 1(iv). The bound material was washed with Buffers A, B and C of increasing pH, and the protein concentration of the effluent fractions was monitored. As seen in FIG. 6, alkaline solutions (Buffer C, pH 10) were required to release the biotinylated protein from the resin.

Figure 7:
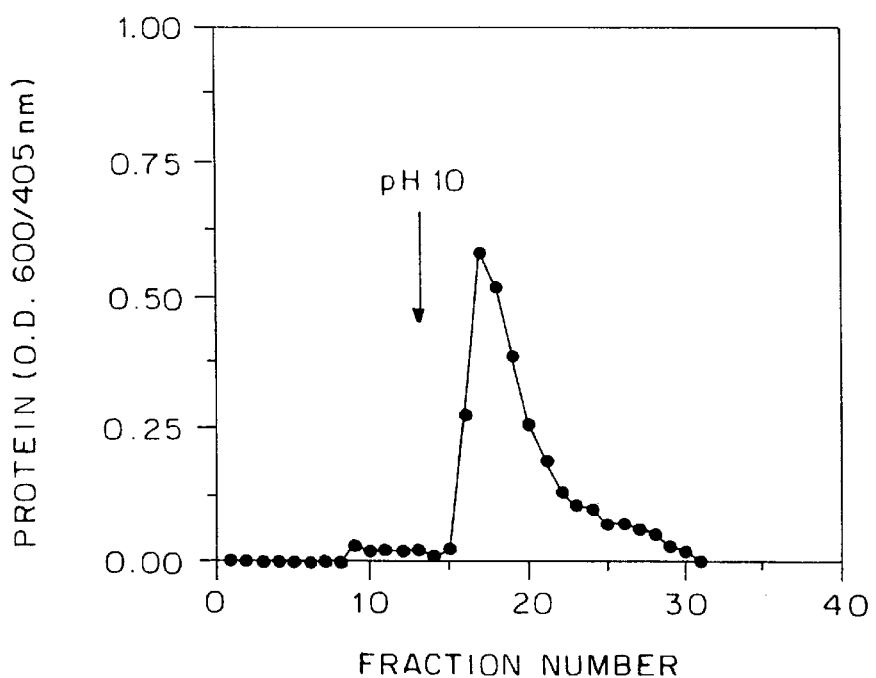
FIG. 7 shows pH-induced release of biotinylated BSA from a Sepharose-nitro-streptavidin resin, as described in Example 3(ii).

(ii) Using the same procedure, but washing only with Buffer C, pH 10, similar results (FIG. 7) were obtained using a nitro-streptavidin column prepared by coupling nitro-streptavidin to Sepharose according to Example 1(iii).

Figure 8:
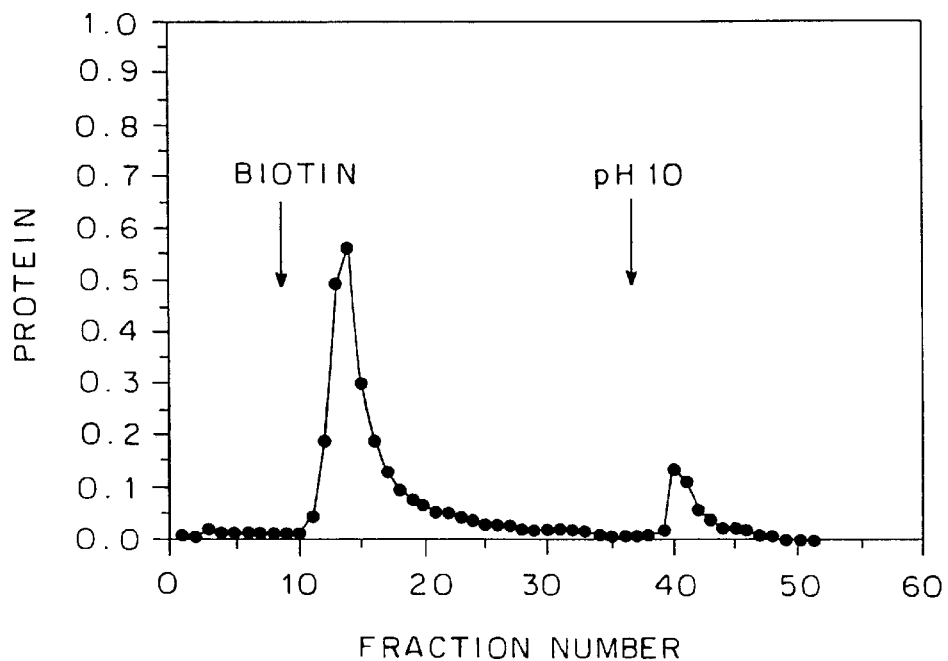
FIG. 8 shows release of biotinylated BSA from a Sepharose-nitro-avidin resin by competition with free biotin, as described in Example 3(iii).

(iii) In a similar experiment, competition with free biotin was explored as a means to release biotinylated BSA from a column containing a nitro-avidin-Sepharose resin prepared according to Example 1(iv). Biotinylated Bsa (1.5 mg/150 µl Buffer A, pH 4) was applied to a 2-ml nitro-avidin-Sepharose column. A solution containing 0.6 mM biotin in Buffer A, pH 4, was passed through the column, and the protein concentration was monitored. As shown in FIG. 8, the majority of biotinyl-BSA could be released using 0.6 mM of biotin in Buffer A at pH 4. The biotin-induced elution of biotinyl-BSA was studied as a function of pH, using buffers A, B or C from pH 4 to 10.

Figure 9:
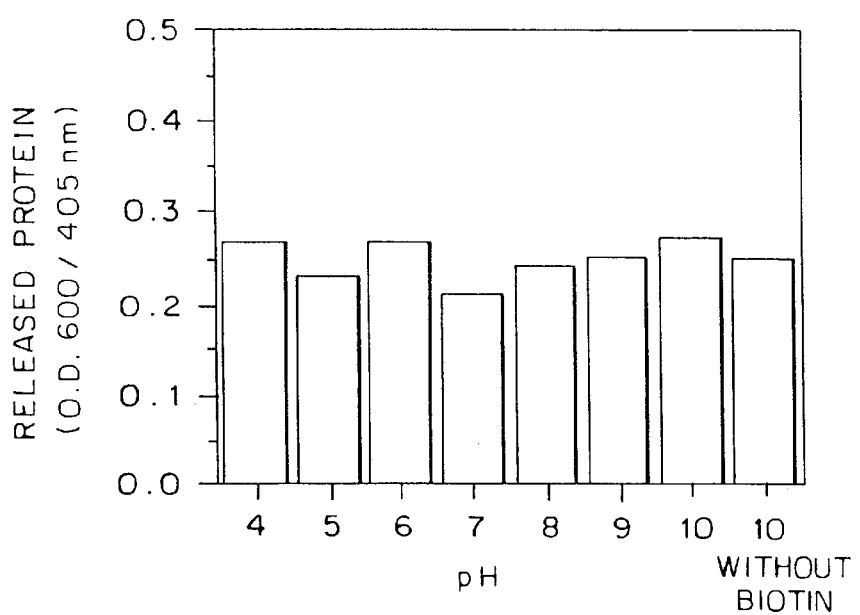
FIG. 9 shows biotin-induced elution of biotinylated BSA as a function of pH, as described in Example 3(iv). The free biotin was dissolved in buffers of different pH, ranging from 4 to 10. Elution of pH 10 in the absence of biotin is shown for comparison.

(iv) A similar experiment was carried out under the same conditions with the nitro-avidin-Sepharose resin prepared according to Example 1(iv), except that the free biotin was dissolved in buffers of different pH ranging from 4 to 10. As shown in FIG. 9, free biotin was an effective eluent over the entire pH range tested. Elution at pH 10 in the absence of biotin is shown for comparison.

Example 4
Blocking of unmodified biotin-binding sites

Figure 10:
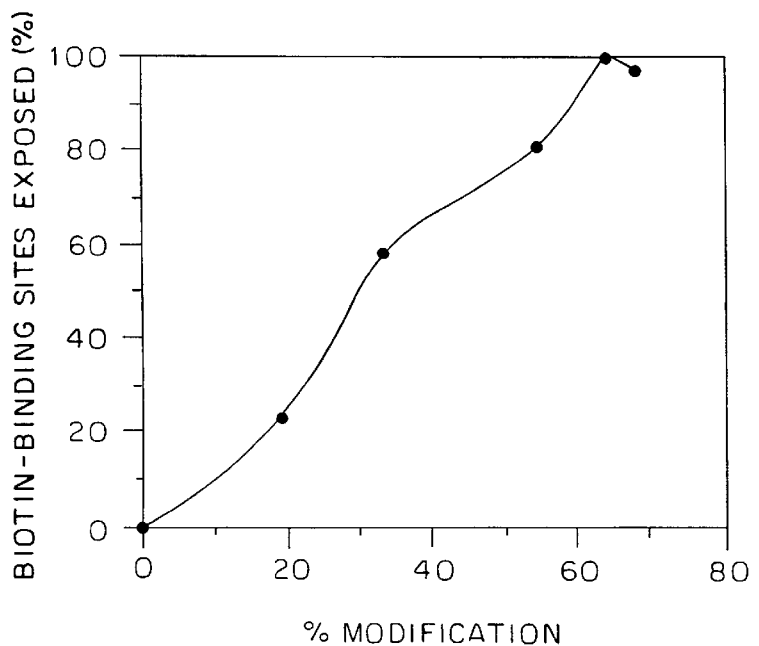
FIG. 10 shows the release of biotin from biotin-blocked sites of nitro-avidin, as described in Example 4.

Since only partial modification of the binding-site tyrosine could be achieved under the described conditions, unmodified sites could potentially pose a problem in subsequent applications of the nitro-avidin. Thus nitro-avidin samples Prepared according to Example 1(i) containing different levels of nitro-tyrosine (see FIG. 2) were coated onto wells of microtiter plates (1 µg/100 µlPBS/well). Native egg-white avidin in similar concentration was used as a control. The wells were blocked with 1% BSA, and the adsorbed protein samples were selectively blocked with excess levels of free biotin using 0.6 mM of biotin in Buffer A, pH 4. The biotin which occupied the modified binding sites could be released using alkaline solutions as described above in Example 3 (Buffer C, pH 10). After blocking and alkaline treatment, the biotin-binding capacity of the partially nitrated avidin samples was determined by enzyme assay in microtiter plates using the biotinylated peroxidase system (method v(a) above). As shown in FIG. 10, the binding was found to be proportional to the extent of modification, with maximum at about 60% modification.

Example 5
Repeated use of nitro-avidin column

Figure 11A:
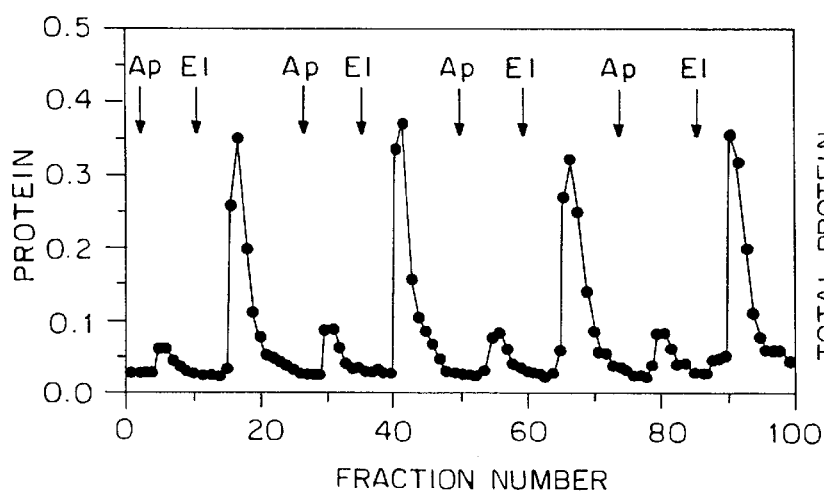
FIGS. 11 A–B show the results of repeated application and elution of biotinylated BSA from a nitro-avidin-Sepharose column, as described in Example 5.
Figure 11B:
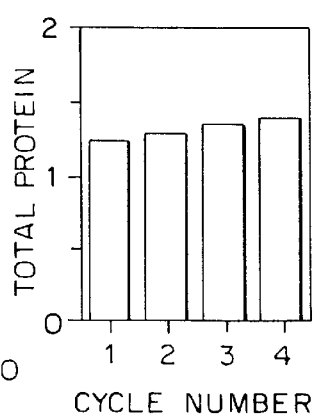

The stability of the column containing a Sepharose-nitro-avidin resin according to Example 1(iii) was tested by repeated application and elution of a biotinylated protein. Identical samples of biotinylated BSA (300 µg/1 ml Buffer A, pH 4) were applied to a 0.75 ml column of the Sepharose-nitro-avidin resin. The column was washed with Buffer A, pH 4, and eluted using Buffer C, pH 10. The procedure was repeated three additional times, and the fractions were monitored for protein by the Bradford assay (FIG. 11A). As shown in FIG. 11B, accumulation of the eluted fractions gave essentially identical levels of biotinylated protein bound to and released from the nitro-avidin column per cycle.

Example 6
Purification of IgG on biotinyl-protein A/nitro-avidin column

Figure 12:
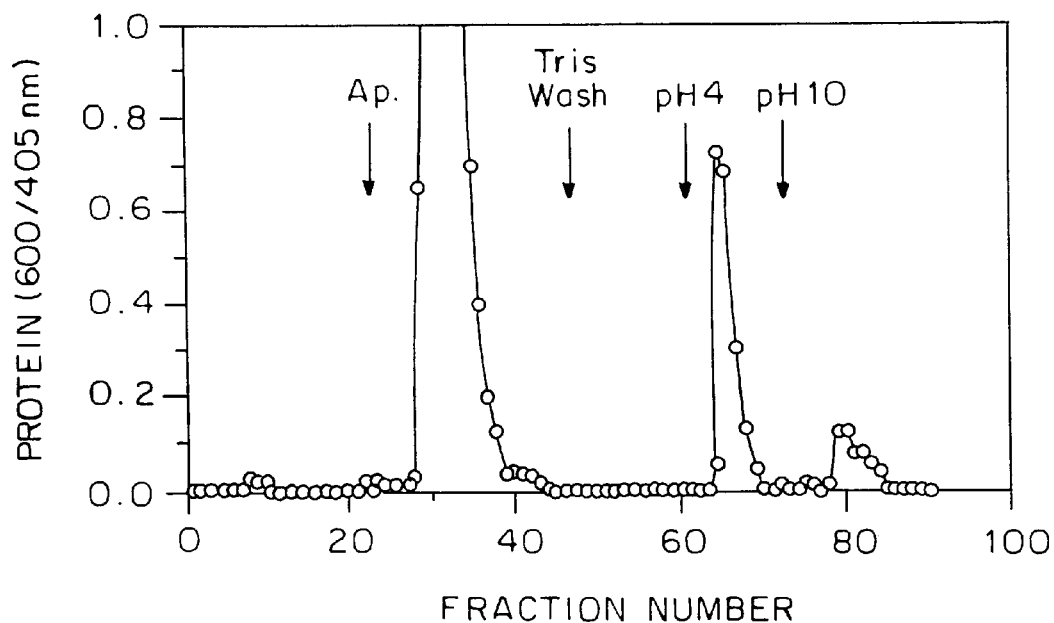
FIG. 12 shows the release of biotinylated protein A from a column containing a Sepharose-nitro-avidin resin following purification of immunoglobulin from whole rabbit serum, as described in Example 6.
Figure 13:
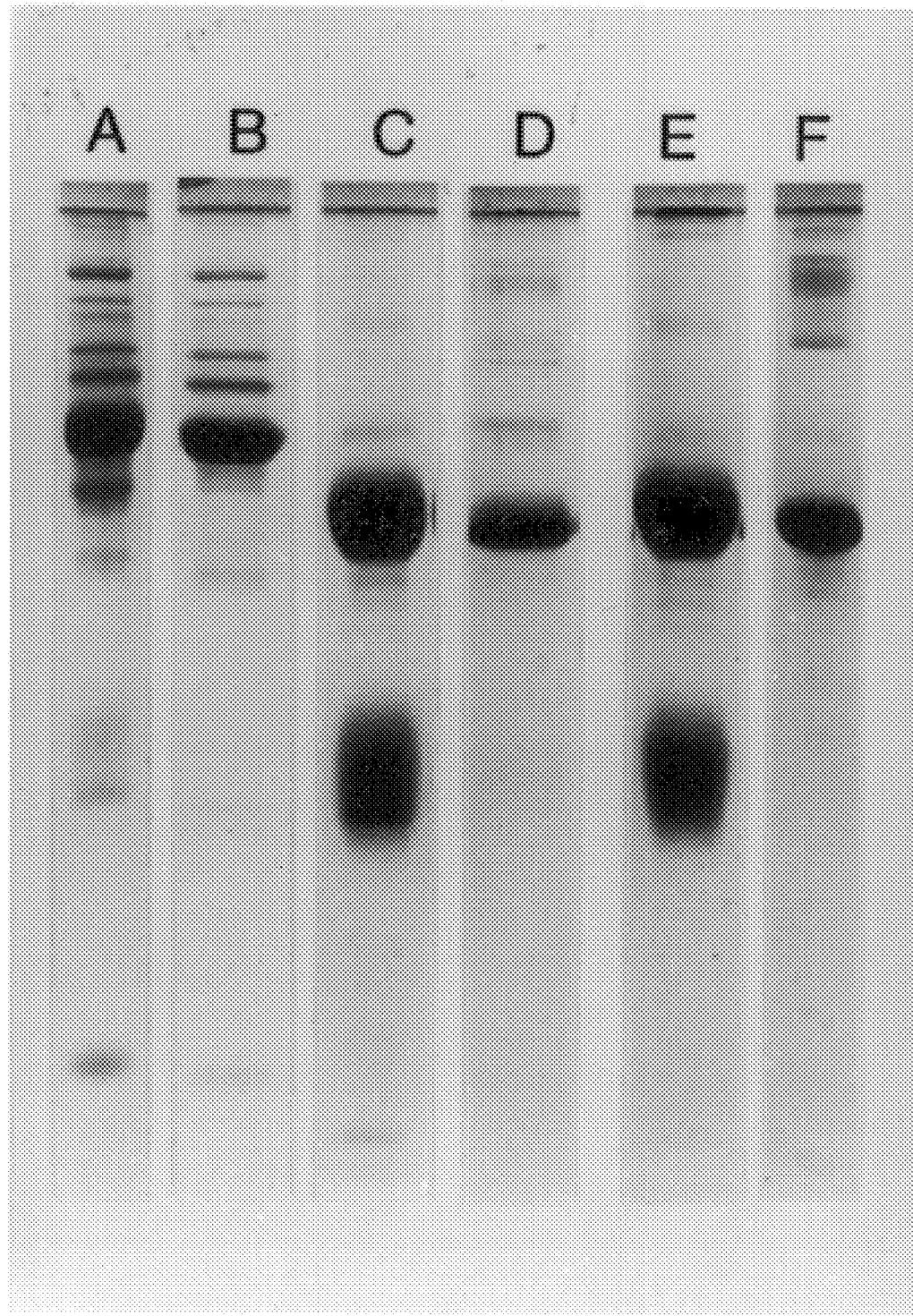
FIG. 13 shows the SDS-PAGE profile of samples from the column in FIG. 12; Lane A, whole rabbit serum (applied fraction); Lane B, column effluent; Lane C, peak eluted by Buffer A, pH 4, Lane D, peak eluted by Buffer C, pH 10; Lane E, commercial preparation of rabbit immunoglobulin; Lane F, biotinylated protein A standard.

The performance of a nitro-avidin column as a universal affinity resin was examined. In this approach, biotinylated protein A was attached to Sepharose and poured into a column, the column was used as an immunoaffinity column in the purification of immunoglobulin directly from whole rabbit serum, and the biotinylated protein A was subsequently released from the column. To a 2-ml column containing 0.5 mg nitro-avidin/ml Sepharose prepared according to Example 1(iv), 1.8 mg of protein A in 4 ml of Buffer A, pH 4, were added. Whole rabbit serum (0.5 ml diluted 4-fold with 0.1M Buffer B, pH 8) was applied to the column. The column was washed with the same buffer, followed by the same buffer at 10 mM concentration. The bound immunoglobulin was released from the column by Buffer A, pH 4. The biotinylated protein A was removed subsequently by 50 mM Buffer C, pH 10. The results are shown in FIG. 12. The various peaks were then examined by SDS-PAGE, which indicated essentially pure fractions of the expected proteins (FIG. 13). The purified immunoglobulin appeared to be as pure as a commercially available sample of an equivalent fraction, and the biotinyl protein A, which eluted from the column by alkaline treatment, was similarly pure.

Example 7
Preparation of iodinated avidin and binding of biotinylated proteins to iodinated avidin adsorbed in microtiter plates (I) Preparation of iodinated avidin. A sample of 2 mg avidin in 0.5 ml sodium phosphate buffer pH 7 was treated with 10 $\mu$l KI solution (32 mg/ml) and 200 $\mu$l of Chloramine-T (2 mg/ml) were added for a period of 1 min. Termination was performed by addition of 1 ml of 1% KI solution. The sample was dialyzed overnight against double-distilled water.

Figure 14:
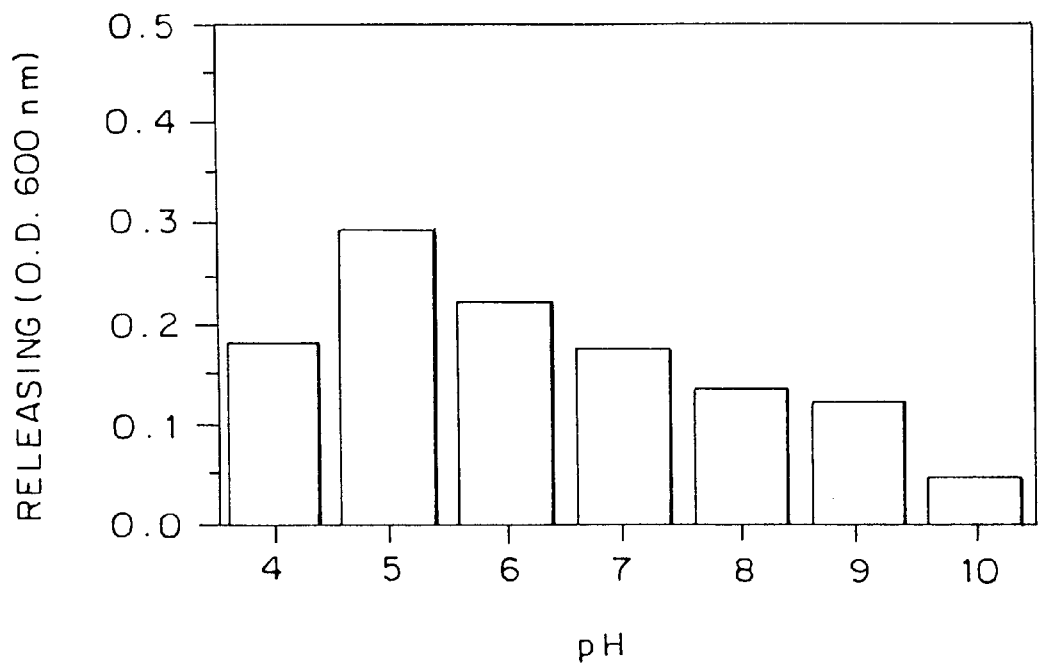
FIG. 14 shows the effect of pH on the releasing of biotinylated horseradish peroxidase from microtiter plates containing adsorbed iodinated avidin, as described in Example 7.

(ii) Binding of biotinylated peroxidase to iodinated avidin. The iodinated avidin was adsorbed to microtiter plates, the plates were blocked by a solution of 1% BSA, and samples of biotinylated horseradish peroxidase were applied in Buffers A, B and C of different pH (37 $\mu$g/0.1 ml buffer/well). The plates were washed and the peroxidase enzymatic activity was determined as described in method v(a) above using ABTS as a substrate. As shown in FIG. 14, optimal binding occurred at pH 5.

Example 8
Preparation of azotyrosine-avidin and streptavidin p-Arsanilic acid (p-aminobenzene arsonic acid) (100 mg) dissolved in 0.3M HCl (10 ml) was treated in an ice-bath with NaNO$_2$ (35 mg in 5 ml water). After 6 min, the solution was adjusted to pH 5 with NaOH, and used immediately. 0.5 ml of the resulting azoarsanilic acid (2 mg in 0.1M sodium borate buffer, pH 8.4) was added to a solution of avidin (5 mg in 4.5 ml of 0.1M sodium borate buffer, pH 8.4), and the reaction was carried out for 2 hours at room temperature. The progress of the reaction was followed spectrophotometrically ($\lambda_{max}$ 342 nm), and the azoarsanylate-derivatized avidin was dialyzed against PBS or 50 mM Tris buffer, pH 8.

Azo-tyrosine streptavidin was prepared in a similar manner.

Substituting p-arsanilic acid by other p-aminobenzene derivatives, e.g. anthranilic acid (o-aminobenzoic acid), p-aminobenzoic acid, p-aminobenzenephosphoric acid and sulfanilic acid (p-aminobenzenesulfonic acid), the corresponding azo derivatives are obtained.

Example 9
Preparation of aminotyrosine-avidin and streptavidin

Nitro-avidin or azotyrosine-avidin (2 mg in 1 ml of 50 mM Tris buffer, pH 8) was treated with a 24-fold molar excess of Na$_2$S$_2$O$_4$ (1.4 mg in 4 ml of the same buffer). The reaction was carried out at room temperature for 16 hours, and the extent of reduction was verified spectrophotometrically (decrease in absorbance at $\lambda_{max}$ 428 nm for nitro-avidin or 342 nm for azotyrosine-avidin). The protein was dialyzed against PBS.

Aminotyrosein-streptavidin was produced by a similar procedure using 1 mg of nitro-streptavidin and a corresponding molar excess of Na$_2$S$_2$O$_4$.

REFERENCES

1. Argarana, C. E., Kuntz, I. D., Birken, S., Axel, R. and Cantor, C. R. (1986) *Nucl. Acids Res.* 14, 1871.

2. Bayer, E. A., Ben-Hur, H. and Wilchek, M. (1990) *Methods Enzymo.* 184, 80.

3. Bayer, E. A., and Wilchek, M. (1990) *Methods Enzymol.* 184, 138.

4. Bayer, E. A. and Wilchek, M. (1992a) *Methods in Molec. Biology* 10, 137.

5. Bayer, E. A. and Wilchek, M. (1992b) *Methods in Molec. Biology* 10, 143.

6. Chandra, G. and Gray, G. (1990) *Methods Enzymol.* 184, 70.

7. Finn, F. M. and Hofmann, K. H. (1985) *Methods Enzymol.* 109, 418.

8. Gitlin, G., Bayer, E. A. and Wilchek, M. (1987) *Biochem. J.* 242, 923.

9. Gitlin, G., Bayer, E. A. and Wilchek, M. (1988a) *Biochem. J.* 250, 291.

10. Gitlin, G., Bayer, E. A. and Wilchek, M. (1988b) *Biochem. J.* 256, 279.

11. Gitlin, G., Khaiy, I., Bayer, E. A., Wilchek, M. and Muszkat, K. A. (1989) *Biochem. J.* 259, 493.

12. Gitlin, G., Bayer, E. A. and Wilchek, M (1990) *Biochem. J.* 269, 527.

13. Gorecki, M., Wilchek, M. and Patchornik, A. (1971) *Biochim. Biophys. Acta* 229, 590–595.

14. Green, N. M. (1975) *Adv. Protein Chem.* 29, 85.

15. Green, N. M. (1990) *Methods Enzymol.* 184, 51.

16. Hiller, Y., Bayer, E. A. and Wilchek, M. (1990) *Methods Enzymol.* 184, 68.

17. Katchalski-Katzir, E. (1993) *TIBTECH* 11, 471.

18. Kohn, J. and Wilchek, M. (1984) *Appl. Biochem. Biotechnol.* 9, 285.

19. Riordan, J. F., Sokolovsky, M. and Vallee, B. L. (1966) *J. Am. Chem. Soc.* 88, 4104.

20. Scott, J. K. (1992) *TIBS* 17, 241.

21. Sokolovsky, M., Riordan, J. F. and Vallee, B. L. (1967) *Biochim. Biophys. Res. Communic.* 27, 20–25.

22. Suter, M., Cazin, Jr. J., Butler, J. E. and Mock, D. M. (1988) *J. Immunol. Meth* 113, 83.

23. Weber. P. C., Ohlendorf, D. H., Wendolosky, J. J. and Salemme, F. R. (1989) *Science* 243, 85.

24. Wilchek, M. and Bayer, E. A. (1988) *Analytical Biochemistry* 171, 1.

25. Wilchek, M. and Bayer, E. A., (1990) "Avidin-Biotin Technology", *Methods in Enzymology,* Vol. 184, Academic Press, Inc., San Diego.

We claim:

1. A biotin-binding modified avidin-type molecule selected from the group of molecules consisting of: (i) native egg-white avidin; (ii) recombinant avidin; (iii) deglycosylated forms of avidin; (iv) bacterial streptavidin; (v) recombinant streptavidin; (vi) truncated streptavidin; and (vii) derivatives of (i)–(vi) which are modified at sites other than at a tyrosine residue, wherein, in said biotin-binding modified avidin-type molecule, the tyrosine residue in the biotin-binding site is modified in such a way that its pKa is decreased in comparison to the pKa of the unmodified tyrosine residue in the corresponding unmodified avidin-type molecule, without inactivating the biotin-binding capability of the molecule.

2. A modified avidin-type molecule according to claim 1, in which the pKa of the tyrosine in the biotin-binding site is decreased by the addition of one or more electrophilic and/or nucleophilic groups on the tyrosine residue.

3. A modified avidin-type molecule according to claim 2, wherein the biotin-binding site of said modified avidin-type molecule has a modified tyrosine residue of the formula:

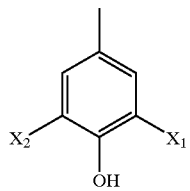

wherein $X_1$ and $X_2$ are each a radical selected from the group consisting of nitro, halogen, $NR_1r_2$ and —N=$NR_3$ in which $R_1$ and $R_2$ are each selected from the group consisting of hydrogen, $C_1$–$C_8$ alkyl and $C_1$–$C_6$ carboxylic acyl, and $R_3$ is aryl substituted by an acidic radical.

4. A modified avidin-type molecule according to claim 3, in which $X_1$ and/or $X_2$ is a nitro group.

5. A modified avidin-type molecule in accordance with claim 1 consisting of nitro-tyrosine native egg-white avidin.

6. A modified avidin-type molecule in accordance with claim 1 consisting of nitro-tyrosine bacterial streptavidin.

7. A method for the preparation of a biotin-binding nitro-tyrosine modified avidin-type molecule according to any one of claim 4, which comprises reacting the unmodified avidin-type molecule with tetranitromethane under nondenaturing conditions.

8. A modified avidin-type molecule according to claim 3, in which $X_1$ and/or $X_2$ is halogen.

9. A modified avidin-type molecule according to claim 8, in which said halogen is iodine.

10. A modified avidin-type molecule according to claim 3, in which $X_1$ and/or $X_2$ is an azo group.

11. A modified avidin-type molecule according to claim 3, in which $X_1$ and/or $X_2$ is an amino group.

12. A modified avidin-type molecule according to claim 3, in which $X_1$ and/or $X_2$ is an —N=$NR_3$ group, in which $R_3$ is phenyl substituted by carboxyl or by an acyl radical derived from an inorganic acid.

13. A modified avidin-type molecule according to any one of claim 1, attached to a solid support.

14. A modified avidin-type molecule according to claim 13, wherein the solid support is a resin, a microtiter plate, glass beads or magnetic beads.

15. A modified avidin-type molecule according to claim 14, wherein the solid support is a resin.

16. A modified avidin-type molecule according to claim 15, wherein the resin is Sepharose.

17. A column for the immobilization of a biotinylated ligand containing a modified avidin-type molecule of claim 1 attached to a resin.

18. A column according to claim 17, wherein said modified avidin-type molecule is nitro-tyrosine native egg-white avidin and said resin is Sepharose.

19. A column according to claim 17, wherein said modified avidin-type molecule is nitro-tyrosine bacterial streptavidin and said resin is Sepharose.

20. In the process for the recovery of either the avidin-column or the biotinylated ligand in a method employing the avidin-biotin technology which comprises:

(i) immobilizing a biotinylated ligand onto a column containing an avidin-type molecule attached to a resin to form an avidin-column;

(ii) carrying out a desired reaction or separation process with the thus immobilized biotinylated ligand;

(iii) removing the biotinylated ligand from the immobilized avidin-column by raising the pH, heating, adding excess concentrations of biotin or low concentrations of urea, guanidine or thiocyanate, and/or combinations thereof; and (iv) recovering the biotinylated ligand and/or the avidin-column for further use, the improvement wherein said avidin-type molecule is a modified avidin-type molecule in accordance with claim 1.

21. A process according to claim 20 wherein the biotinylated ligand is removed from the immobilized modified avidin-column by raising the pH to 10.

22. A process according to claim 20 wherein the biotinylated ligand is removed from the immobilized modified avidin-column by adding 0.6 mM biotin.

23. A process according to claim 20 wherein the biotin-binding site of said modified avidin-type molecule has a modified tyrosine residue of the formula:

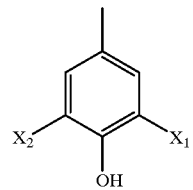

wherein $X_1$ and $X_2$ are each a radical selected from the group consisting of nitro, halogen, $NR_1R_2$ and —N=$NR_3$ in which $R_1$ and $R_2$ are each hydrogen, $C_1$–$C_8$ alkyl or $C_1$–$C_6$ carboxylic acyl, and $R_3$ is aryl substituted by an acidic radical.

24. A process according to claim 20 wherein said modified avidin-type molecule is nitro-tyrosine native egg-white avidin.

25. A process according to claim 20 wherein said modified avidin-type molecule is nitro-tyrosine bacterial streptavidin.

26. In a chemical or biochemical process using avidin-biotin technology, the improvement wherein the avidin used in said avidin-biotin technology is a modified avidin-type molecule in accordance with claim 1.

27. A chemical or biochemical process using avidin-biotin technology, in accordance with claim 26, wherein said process is a method of affinity chromatography, cell separation, cell immobilization and release, capture and release of DNA, immobilization and release of biotinylated enzymes, production of phage libraries, or production of reversible matrices for biosensors.

28. A modified avidin-type molecule according to claim 1, wherein said tyrosine residue is modified without modifying the tyrosine hydroxyl group.

* * * * *